United States Patent
Terada et al.

(10) Patent No.: US 10,254,254 B2
(45) Date of Patent: Apr. 9, 2019

(54) PREPARATIVE SEPARATION LIQUID CHROMATOGRAPH SYSTEM AND PREPARATIVE SEPARATION CONDITION SEARCHING METHOD

(71) Applicant: Shimadzu Corporation, Kyoto-shi, Kyoto (JP)

(72) Inventors: Hidetoshi Terada, Kyoto (JP); Yuji Katsuyama, Kyoto (JP); Katsuhiko Miwa, Fujisawa (JP); Chie Kushibe, Fujisawa (JP)

(73) Assignee: SHIMADZU CORPORATION, Kyoto-shi, Kyoto (JP)

( * ) Notice: Subject to any disclaimer, the term of this patent is extended or adjusted under 35 U.S.C. 154(b) by 229 days.

(21) Appl. No.: 15/502,222

(22) PCT Filed: Aug. 7, 2015

(86) PCT No.: PCT/JP2015/072483
§ 371 (c)(1),
(2) Date: Feb. 7, 2017

(87) PCT Pub. No.: WO2016/021715
PCT Pub. Date: Feb. 11, 2016

(65) Prior Publication Data
US 2017/0234839 A1 Aug. 17, 2017

(30) Foreign Application Priority Data
Aug. 8, 2014 (JP) .................................. 2014-162219

(51) Int. Cl.
*G01N 30/14* (2006.01)
*G01N 30/46* (2006.01)
(Continued)

(52) U.S. Cl.
CPC ............. *G01N 30/14* (2013.01); *G01N 30/24* (2013.01); *G01N 30/46* (2013.01); *G01N 30/80* (2013.01);
(Continued)

(58) Field of Classification Search
CPC .... B01D 15/1885; G01N 30/14; G01N 30/24; G01N 30/46; G01N 30/466; G01N 30/80; G01N 30/82; G01N 30/86; G01N 30/8658
See application file for complete search history.

(56) References Cited

U.S. PATENT DOCUMENTS 4,724,081 A * 2/1988 Kawahara .......... B01D 15/1814
 210/198.2
6,280,627 B1 * 8/2001 Kobayashi ............. G01N 30/82
 210/656
(Continued)

FOREIGN PATENT DOCUMENTS

JP 2000-214151 A 8/2000

OTHER PUBLICATIONS

Written Opinion for PCT/JP2015/072483 dated Sep. 29, 2015. [PCT/ISA/237].
(Continued)

*Primary Examiner* — Randy W Gibson
*Assistant Examiner* — Gedeon M Kidanu
(74) *Attorney, Agent, or Firm* — Sughrue Mion, PLLC

(57) ABSTRACT

Provided is a preparative separation liquid chromatograph system and preparative separation condition searching method which allows for an easy setting of the preparative separation condition. A sample temporally separated into components by a separation column is introduced into a detector and a fraction collector, with each component fractionated and collected by the fraction collector based on (Continued)

the result of a detection by the detector. A controlling and processing unit holds the following data for each sample or compound in the form of a database: chromatogram data obtained when a liquid chromatograph analysis in a preparative separation condition searching mode is performed for various standard samples under a search condition; and chromatogram data obtained when a liquid chromatograph analysis in a preparative separation mode is performed under one or more sets of preparative separation conditions for the various standard samples, along with the preparative separation condition used in this analysis.

12 Claims, 12 Drawing Sheets

(51) Int. Cl.
    *B01D 15/18*     (2006.01)
    *G01N 30/80*     (2006.01)
    *G01N 30/86*     (2006.01)
    *G01N 30/24*     (2006.01)
    *G01N 30/82*     (2006.01)

(52) U.S. Cl.
    CPC ............ *G01N 30/82* (2013.01); *G01N 30/86* (2013.01); *G01N 30/8658* (2013.01); *B01D 15/1885* (2013.01); *G01N 30/466* (2013.01)

(56) References Cited

U.S. PATENT DOCUMENTS

| | | | | |
|---|---|---|---|---|
| 6,737,022 B1* | 5/2004 | Sutton | ................. | B01D 15/247 222/630 |
| 7,022,239 B2* | 4/2006 | Heikkila | ............ | B01D 15/1821 127/46.2 |
| 8,932,460 B2* | 1/2015 | Yamazaki | .............. | G01N 30/08 210/198.2 |
| 10,048,237 B2* | 8/2018 | Mito | .................. | G01N 30/8631 |
| 2004/0018118 A1* | 1/2004 | Waki | .................... | B01D 15/247 422/70 |
| 2006/0121559 A1* | 6/2006 | Takaki | ................. | B01J 20/3242 435/68.1 |
| 2009/0314716 A1* | 12/2009 | Osaka | .................... | G01N 30/82 210/656 |
| 2010/0276350 A1* | 11/2010 | Kono | ................... | B01D 15/166 210/198.2 |
| 2010/0281958 A1* | 11/2010 | Kono | ................... | B01D 15/203 73/61.53 |
| 2011/0184658 A1* | 7/2011 | Maruyama | ............. | G01N 30/82 702/25 |
| 2014/0182396 A1* | 7/2014 | Okoba | ............... | G01N 35/1016 73/863.01 |
| 2014/0244185 A1* | 8/2014 | Yamamura | .......... | H01J 49/0036 702/23 |
| 2014/0303903 A1* | 10/2014 | Fujita | .................. | H01J 49/0036 702/23 |
| 2015/0066388 A1* | 3/2015 | Katsuyama | ............ | G01N 30/24 702/31 |
| 2015/0293064 A1* | 10/2015 | Aota | ....................... | G01N 30/34 73/61.52 |
| 2015/0377843 A1* | 12/2015 | Morikawa | .............. | G01N 30/24 73/863.02 |
| 2016/0018370 A1* | 1/2016 | Mito | .................. | G01N 30/8631 73/61.56 |
| 2016/0202854 A1* | 7/2016 | Minato | ................. | G06F 3/0482 715/773 |
| 2016/0216239 A1* | 7/2016 | Aota | ...................... | G01N 30/26 |

OTHER PUBLICATIONS

International Search Report for PCT/JP2015/072483 dated Sep. 29, 2015 [PCT/ISA/210].

* cited by examiner

Fig. 2A
ANALYSIS CONDITIONS

| KIND OF COLUMN | L-column2 ODS, MANUFACTURED BY CHEMICALS EVALUATION AND RESEARCH INSTITUTE, JAPAN (3.0mm I.D. × 50mm L. 3 μm) |
|---|---|
| MOBILE PHASE | A: 5mmol/L AQUEOUS SOLUTION OF AMMONIUM BICARBONATE<br>B: ACETONITRILE |
| FLOW RATE | 1.5 mL/min |
| TEMPERATURE | 40°C |
| INJECTION AMOUNT | 2 μL (0.1mg/mL PER COMPONENT) |
| DETECTION WAVELENGTH | 220nm |

Fig. 2B
LIQUID-SENDING SCHEDULE

| TIME (min) | ACETONITRILE CONCENTRATION (%) |
|---|---|
| 0 | 5 |
| 1 | 90 |
| 2 | 90 |
| 2.01 | 5 |
| 3 | STOP |

CHROMATOGRAM OF EACH COMPONENT

RETENTION TIME OF EACH COMPONENT

| COMPONENT | R.T.(min) |
|---|---|
| Phenol | 0.918 |
| 2,6-Dimethylaniline | 1.130 |
| Benzene | 1.248 |
| Verapamil | 1.408 |
| Ethylbenzene | 1.451 |
| Nicardipine | 1.493 |

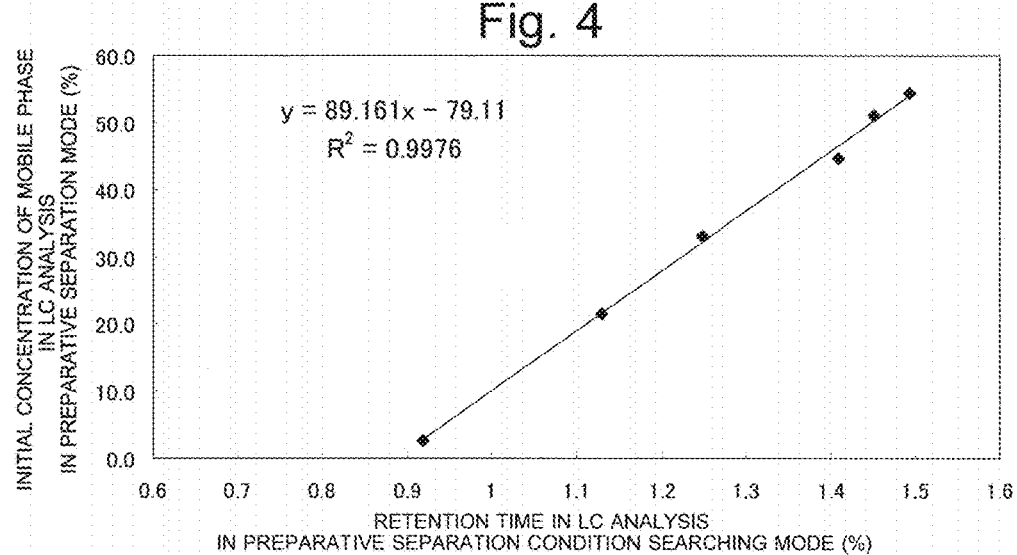

Fig. 4

Fig. 5A  PREPARATIVE SEPARATION CONDITIONS

| | |
|---|---|
| KIND OF COLUMN | L-column2 ODS, MANUFACTURED BY CHEMICALS EVALUATION AND RESEARCH INSTITUTE, JAPAN (20mm I.D. ×50mm L. 5μm) |
| MOBILE PHASE | A: 10mmol/L AQUEOUS SOLUTION OF AMMONIUM BICARBONATE<br>B: ACETONITRILE |
| FLOW RATE | 20 mL/min |
| TEMPERATURE | ROOM TEMPERATURE |
| INJECTION AMOUNT | 100~1000 μL (1~5mg/mL PER COMPONENT) |
| DETECTION WAVELENGTH | 220nm |

Fig. 5B  LIQUID-SENDING SCHEDULE

| TIME (min) | ACETONITRILE CONCENTRATION (%) |
|---|---|
| 0 | X |
| 4 | X+20 |
| 4.01 | 90 |
| 7 | STOP |

(a) Phenol

| INITIAL CONCEN-TRATION (%) | R.T. (min) |
|---|---|
| 3 | 3.954 |
| 6 | 3.544 |

(b) RESULT

TIME (min)

(a) 2,6-Dimethylaniline

| INITIAL CONCEN-TRATION (%) | R.T. (min) |
|---|---|
| 19 | 4.316 |
| 24 | 3.676 |

(b) RESULT

Fig. 12

| Component | Retention time obtained in the LC analysis in the preparative separation condition searching mode (min) | Initial concentration (%) of the eluate near the target elution time in the LC analysis in the preparative separation mode, and the result of a study on the retention time obtained under the conditions concerned | | Coefficients of the approximate equation showing the relationship between the initial concentration (%) of the eluate near the target elution time in the LC analysis in the preparative separation mode and the retention time (min) | | Calculated value of the initial concentration (%) of the mobile phase eluted at the target elution time in the LC analysis in the preparative separation mode |
|---|---|---|---|---|---|---|
| | | Initial concentration (%) | Retention time (min) | α | β | |
| Phenol | 0.918 | 3 | 3.954 | -0.137 | 4.36 | 2.7 |
| | | 6 | 3.544 | | | |
| 2.6-Dimethylaniline | 1.13 | 19 | 4.316 | -0.128 | 6.75 | 21.5 |
| | | 24 | 3.876 | | | |
| Benzene | 1.248 | 30 | 4.394 | -0.128 | 8.22 | 33.1 |
| | | 34 | 3.884 | | | |
| Verapamil | 1.408 | 45 | 3.973 | -0.120 | 9.38 | 44.7 |
| | | 48 | 3.578 | | | |
| | | 53 | 3.004 | | | |
| Ethylbenzene | 1.451 | 52 | 3.872 | -0.123 | 10.27 | 51.0 |
| | | 50 | 4.118 | | | |
| Nicardipine | 1.493 | 50 | 4.631 | -0.143 | 11.78 | 54.4 |
| | | 53 | 4.193 | | | |
| | | 55 | 3.917 | | | |

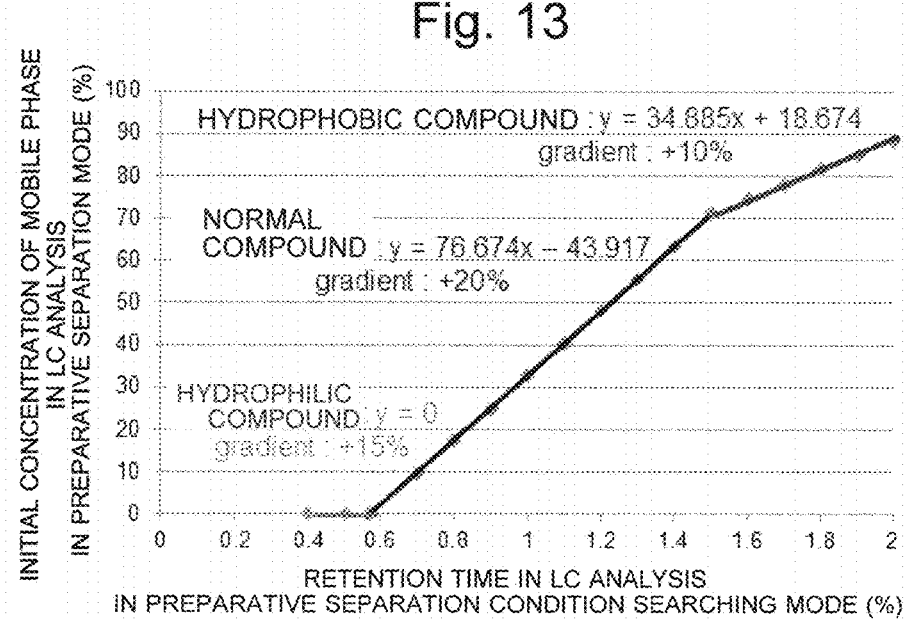

Fig. 13

PREPARATIVE SEPARATION LIQUID CHROMATOGRAPH SYSTEM AND PREPARATIVE SEPARATION CONDITION SEARCHING METHOD

CROSS REFERENCE TO RELATED APPLICATIONS

This application is a National Stage of International Application No. PCT/JP2015/072483, filed on Aug. 7, 2015, which claims priority from Japanese Patent Application No. 2014-162219, filed on Aug. 8, 2014, the contents of all of which are incorporated herein by reference in their entirety.

TECHNICAL FIELD

The present invention relates to a preparative separation liquid chromatograph system and preparative separation condition searching method for separating and collecting one or more components contained in a sample using a liquid chromatograph.

BACKGROUND ART

A preparative separation liquid chromatograph system is an application technique of a liquid chromatograph (which is hereinafter abbreviated as "LC"), in which a fraction collector is provided on the downward side of the LC passage so as to separate one or more target components contained in a sample and selectively collect each component (for example, see Patent Literature 1).

In the preparative separation liquid chromatograph system, the sample is passed through a column with the mobile phase to temporally separate the target components. The separated target components are detected with a detector (e.g. spectrophotometer) provided on the downward side of the column, and a chromatogram is created based on the detection signals. A peak which appears on the chromatograph is located from the waveform of the chromatogram. With the beginning and ending of the peak, an electromagnetic valve (or similar device) in the fraction collector is opened or closed, whereby the target components are individually collected into separate vials.

For the preparative separation of the target components using such a preparative separation liquid chromatograph system, it is necessary to appropriately set preparative separation conditions for each sample or target compound, such as the kind of column, kind of mobile phase, and flow rate/flow velocity of the mobile phase. To this end, an LC analysis is performed under various conditions for each sample or target compound to search for optimum preparative separation conditions.

CITATION LIST

Patent Literature

Patent Literature 1: JP 2000-214151 A

SUMMARY OF INVENTION

Technical Problem

In order to suppress the amount of sample used for the search of the preparative separation conditions, a method has conventionally been used in which optimum conditions in an LC analysis using a column having a smaller capacity than the column for the preparative separation are determined, and the obtained result is adjusted for an analyzing system using the preparative separation column to determine the final preparative separation conditions. The adjusting process is not a simple scaling of the analysis conditions obtained by using the low capacity column; the analysis conditions are determined by repeating the task of performing an LC analysis using the preparative separation column while gradually changing the analysis conditions, and subsequently adjusting the conditions based on the obtained result. Therefore, the task of determining the preparative separation conditions by the aforementioned conventional method is difficult for unskilled persons who do not have a high degree of knowledge on LC analyses, such as the nature of the column (stationary phase) and mobile phase as well as the suitability of the column and/or mobile phase for specific samples (target components).

Furthermore, in the pharmaceutical industries or similar areas, when various compounds (target components) obtained by chemical syntheses need to be preparative-separated from a solution (sample), there are a wide variety of compounds to be separated, and the task of finding appropriate conditions for each compound is extremely cumbersome and tune-consuming even for an expert.

The problem to be solved by the present invention is to provide a preparative separation liquid chromatograph system and a preparative separation condition searching method with which even a user who does not have a high degree of knowledge regarding liquid chromatograph analysis can easily set preparative separation conditions.

Solution to Problem

The first aspect of the present invention developed for solving the previously described problem is a preparative separation liquid chromatograph system in which a sample temporally separated into components by a liquid chromatograph analysis is introduced into a detector and a fraction collector, with each component fractionated and collected by the fraction collector based on the result of a detection by the detector, the system including:

a) a chromatographing section having a preparative separation mode for performing a liquid chromatograph analysis using a column for preparative separation and a preparative separation condition searching mode for performing a liquid chromatograph analysis using a column for searching for a preparative separation condition having a different capacity from the column for preparative separation;

b) a chromatogram creating section for creating a chromatogram based on a detection signal from the detector;

c) a storage section for storing the following data on various standard samples for each sample or compound in the form of a database: chromatogram data obtained when the liquid chromatograph analysis in the preparative separation condition searching mode is performed for the various standard samples under a search condition; and chromatogram data obtained when the liquid chromatograph analysis in the preparative separation mode is performed for the various standard samples under one or a plurality of sets of preparative separation conditions, along with the preparative separation condition used in this analysis;

d) an index input section for allowing a user to input an index concerning a chromatogram for a target sample, the index used for determining the preparative separation condition used when separating the target sample into components by the liquid chromatograph analysis in the preparative separation mode and separately collecting each component; and e) a preparative separation condition determining section for making the chromatographing section perform the liquid chromatograph analysis in the preparative separation condition searching mode for the target sample, and for determining the preparative separation condition for a component contained in the target sample, based on the chromatogram data obtained by this analysis and the aforementioned index, with reference to the database.

The second aspect of the present invention is a preparative separation condition searching method for searching for a preparative separation condition used in a process in which a sample temporally separated into components by a liquid chromatograph analysis is introduced into a detector and a fraction collector, with each component fractionated and collected by the fraction collector based on the result of a detection by the detector; the method including:

a) a storage process in which the following data on various standard samples are stored for each sample or compound in the form of a database: chromatogram data obtained when a liquid chromatograph analysis in a preparative separation mode using a column for preparative separation is performed for the various standard samples; and chromatogram data obtained when a liquid chromatograph analysis in a preparative separation condition searching mode using a column for searching for a preparative separation condition having a different capacity from the column for preparative separation is performed for the various standard samples;

b) an index input process in which a user is allowed to input an index concerning a chromatogram for a target sample, the index used for determining the preparative separation condition used when separating the target sample into components by the liquid chromatograph analysis in the preparative separation mode and for separately collecting each component;

c) a data obtaining process in which the liquid chromatograph analysis in the preparative separation condition searching mode is performed for the target sample to obtain chromatogram data of the target sample; and d) a condition determining process in which the preparative separation condition for a component contained in the target sample is determined based on the chromatogram data of the target sample and the aforementioned index, with reference to the database.

In the present invention, the "chromatogram data" mean not only a set of data used for creating a chromatogram, but also the chromatogram itself.

The column used as the column for searching for a preparative separation condition normally has a lower capacity than the column for preparative separation, although the present invention can also be applied in the case of using a column having a higher capacity than the column for preparative separation.

Examples of the search condition and preparative separation condition include the kind of mobile phase, flow rate of the mobile phase and fluid pressure of the mobile phase. In the case where the liquid chromatograph analysis is performed as a so-called "gradient analysis" in which a mobile phase composed of a mixture of solvents with different natures (e.g. water and an organic solvent) is supplied to the column with the mixture ratio of those solvents gradually changed with the passage of time, the search condition and preparative separation condition also include the mixture ratio of the solvents, initial concentration of a specific solvent, and other related parameters.

Examples of the index concerning the chromatogram used for determining the preparative separation condition include the retention time, elution beginning time and elution completion time of each component determined from the chromatogram. The number of indices is not limited to one but may be two or more. By extracting the preparative separation condition based on a plurality of indices, a more suitable preparative separation condition can be determined for the components in the sample.

In the case of using the elution beginning time as the index, it is preferable to store, in the form of a database in the storage section, the elution beginning time of each component determined from the chromatogram data obtained by the liquid chromatograph analysis in the preparative separation mode performed for various samples, along with the preparative separation condition used in this analysis.

In this configuration, when the elution beginning time is inputted as the index by a user through the index input section, the preparative separation condition determining section refers to the database and extracts an optimum preparative separation condition based on the chromatogram data obtained by the liquid chromatogram analysis in the preparative separation condition searching mode for the target sample as well as the inputted elution beginning time.

Advantageous Effects of the Invention

According to the present invention, once a liquid chromatograph analysis in the preparative separation condition searching mode is performed for a target sample, the preparative separation condition suitable for the target sample can be determined based on the chromatogram obtained in that analysis. Even a user who does not have a high degree of knowledge on the liquid chromatograph analysis or compounds can easily set the preparative separation condition.

BRIEF DESCRIPTION OF DRAWINGS

FIGS. 2A and 2B respectively show the analysis conditions and liquid-sending schedule of an LC analysis in the preparative separation condition searching mode.

FIG. 4 shows a computing equation expressing the relationship between the retention time obtained in the preparative separation condition searching mode and the initial concentration of the mobile phase in the preparative separation mode, as well as a graph representing the same equation.

FIGS. 5A and 5B respectively show the analysis conditions and liquid-sending schedule of an LC analysis in the preparative separation mode performed for determining the computing equation expressing the relationship between the retention time obtained in the preparative separation condition searching anode and the initial concentration of the mobile phase in the preparative separation mode.

FIG. 12 shows the retention time of each compound, initial concentration and elution time of the mobile phase in the preparative separation mode, coefficients of an approximate equation, and estimated initial concentration of the mobile phase.

FIG. 13 shows a variation, in which the compounds are divided into three classes according to their affinity to water, and a different computing equation is set for each class, with each computing equation expressing the retention time obtained in the preparative separation condition searching mode and the initial concentration of the mobile phase, and the graph representing those computing equations.

DESCRIPTION OF EMBODIMENTS

Figure 1:
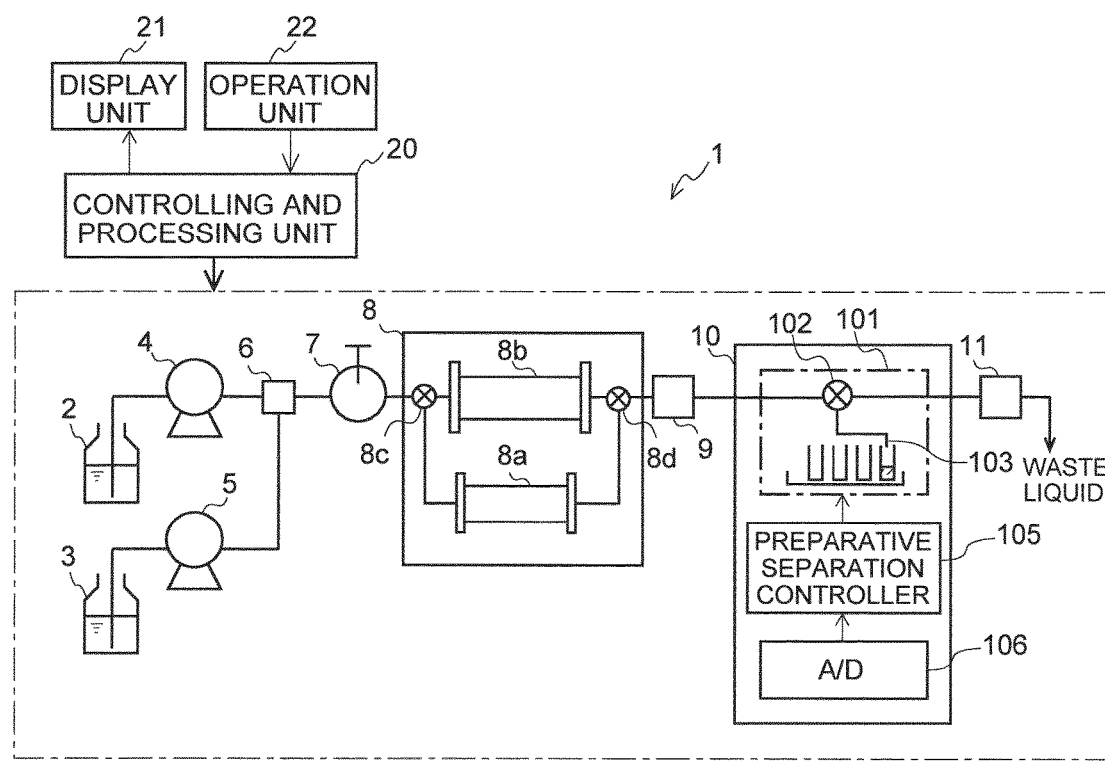
FIG. 1 is a schematic configuration diagram of a preparative separation LC according to one embodiment of the present invention.

A preparative separation liquid chromatograph system as one embodiment of the present invention (which is hereinafter called the "preparative separation LC") is described with reference to the attached drawings. FIG. 1 is a schematic configuration diagram of the preparative separation LC according to the present embodiment.

The preparative separation LC 1 includes first and second liquid-sending pumps 4 and 5, injector 7, separation column 8, first detector 9, fraction collector 10, second detector 11 and other elements. The first liquid-sending pump 4 suctions and supplies a first mobile phase (e.g. water or buffer solution) prepared in a first mobile phase container 2, while the second liquid-sending pump 5 suctions and supplies a second mobile phase which is an organic solvent (e.g. acetonitrile) prepared in a second mobile phase container 3. The first and second mobile phases are mixed by a mixer 6 and supplied to the separation column 8 through the injector 7. The separation column 8, which is provided to separate various components (compounds) in a sample, is composed of multiple kinds of columns, including a column 8a used for an LC analysis in the preparative separation condition searching mode and a column 8b used for an LC analysis in the preparative separation mode, as well as passage switching valves 8c and 8d. The separation column used as the column 8a used for the preparative separation condition searching anode (which is hereinafter called the "preparative separation condition search column") has a lower capacity than the column 8b used for the preparative separation mode (which is hereinafter called the "preparative separation column").

In the present embodiment, the first and second liquid-sending pumps 4 and 5 can be controlled so that their flow velocities independently change with the passage of time, making it possible to supply the liquid in a high-pressure gradient mode in which the composition ratio of the first and second mobile phases changes over time. Needless to say, a single mobile phase may be used instead of performing the gradient liquid supply. Using a mobile phase with a constant composition ratio is also possible.

In the injector 7, a liquid sample selected by an autosampler is automatically injected into the mobile phase at a predetermined timing. The liquid sample is carried by the mobile phase into the separation column 8. While passing through the separation column 8, the various components (compounds) in the liquid sample are temporally separated and eluted from the exit end of the separation column 8. As the first detector 9, which is provided in the downstream area from the separation column 8, for example, an ultraviolet-visible spectrometric detector can be used. The fraction collector 10 is connected to the exit side of the first detector 9. The fraction collector 10 separately collects fractions of the eluate, with each fraction containing one of the target components contained in the eluate. It includes a preparative separator 101 (which includes a preparative separation valve 102, preparative separation nozzle 103 and other elements), preparative separation controller 105, and A/D converter 106.

The second detector 11 is used for verifying preparative separation conditions by investigating whether or not a target compound is contained in the solution which has passed through the preparative separation valve 102. As the second detector 11, a mass spectrometer may be used as well as an ultraviolet-visible spectrometric detector.

The preparative separation LC 1 also has a controlling and processing unit 20 for generally controlling the operation of each section and for processing data. Connected to this controlling and processing unit 20 is a display unit 21 and operation unit 22, such as a keyboard.

The controlling and processing unit 20, which includes a CPU and other elements, controls the on/off operation and liquid-sending speed of the liquid-sending pumps 4 and 5, operation of the injector 7, operation of the passage switching valves 8c and 8d in the separation column 8, as well as other operations according to a previously set program while monitoring the detection signal from the first detector 9. In the present embodiment, the controlling and processing unit 20 functions as the chromatographing section, chromatogram creating section, storage section and preparative separation condition determining section, as will be described later in detail.

In the fraction collector 10, the preparative separation controller 105 has the function of controlling the operation of the preparative separator 101 based on the detection signal (chromatogram signal) obtained with the first detector 9. This function may be built in the controlling and processing unit 20. Additionally, the preparative separation controller 105 in the present embodiment also has the function of calculating the volume of the preparative separation, which function may also be built in the controlling and processing unit 20.

Hereinafter, the characteristic operation of the preparative separation LC 1 of the present embodiment is described.

When the preparative separation condition searching mode is set by an operation on the operation unit 22 by a user, a preparative separation condition setting window (not shown) is displayed on the screen of the display unit 21. After the name of the compound to be preparative-separated and the elution time as the target are set on this preparative separation condition setting window, when a command for initiating the analysis is issued, the sample is introduced into the preparative separation condition search column 8a along with the mobile phase. The sample components separated by the preparative separation condition search column 8a are detected by the first detector 9. Based on the detection signals, a chromatogram is created.

In the present embodiment, the conditions of the LC analysis in the preparative separation condition searching mode (such as the kinds of separation column and mobile phase, operating conditions of the liquid-sending pumps 4 and 5 (liquid-sending schedule and flow rate), and other parameters) are specified in a set of comprehensive conditions that can be generally applied in LC analyses of various compounds. It is also possible to select specific conditions suited for the compound to be preparative-separated from a plurality of sets of analysis conditions. FIG. 2A shows one example of the analysis conditions of the LC analysis in the preparative separation condition searching mode, and FIG. 2B shows one example of the liquid-sending schedule.

Subsequently, the controlling and processing unit 20 extracts the peak of each compound from the obtained chromatogram, determines its retention time (R.T.), and sets the preparative separation conditions based on the retention time as well as the target elution time previously set on the preparative separation condition setting window. The set preparative separation conditions are displayed on the preparative separation condition setting window.

Figures 3A, 3B:
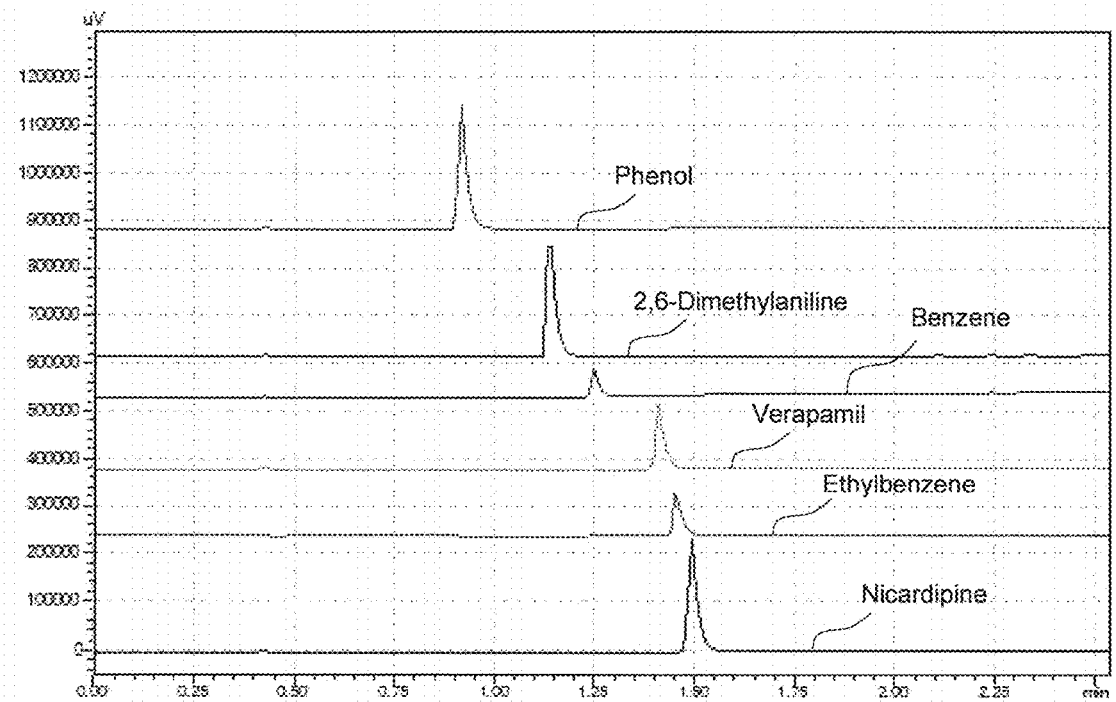
FIG. 3A is a chromatogram showing the result of an LC analysis in the preparative separation condition searching mode.
FIG. 3B shows the retention time of each compound.
Figure 6:
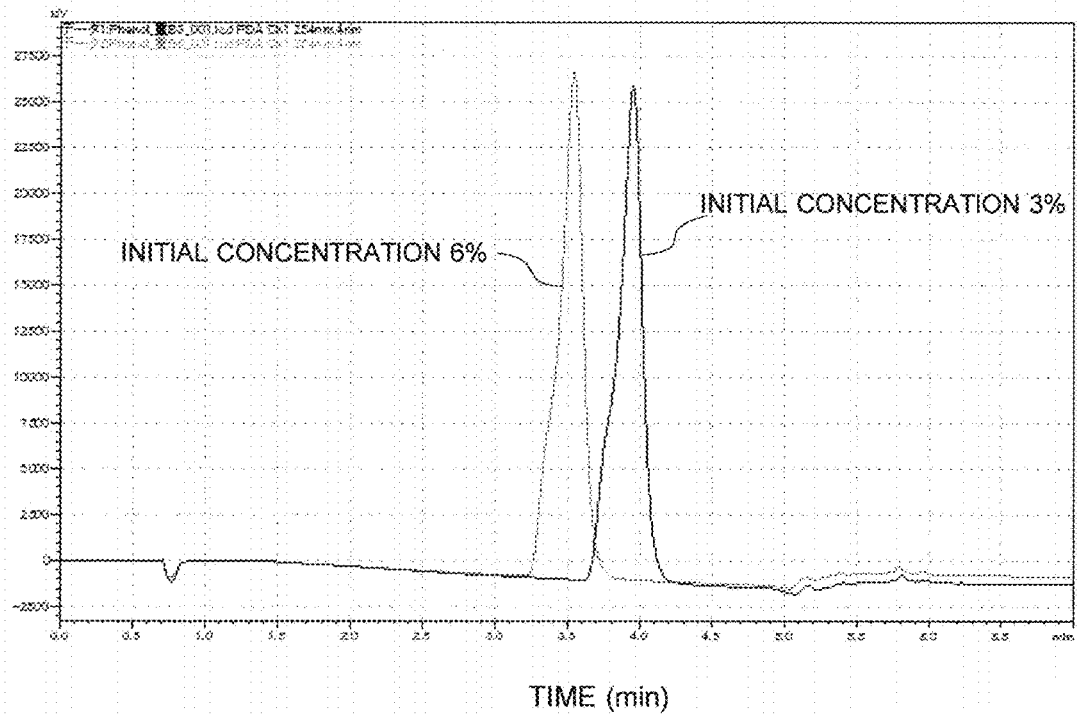
FIG. 6 shows a table (a) and chromatogram (b) illustrating the relationship between the initial concentration of the mobile phase and the retention time, with phenol as the sample.
Figure 7:
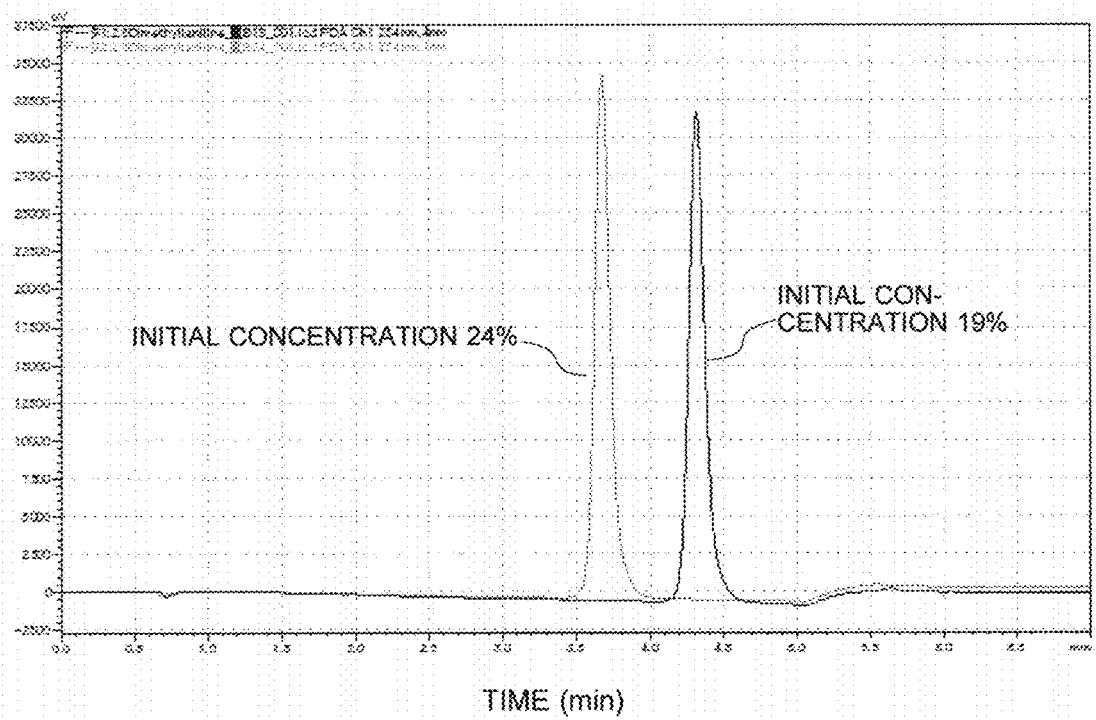
FIG. 7 shows a table (a) and chromatogram (b) illustrating the relationship between the initial concentration of the mobile phase and the retention time, with dimethylaniline as the sample.
Figure 8:
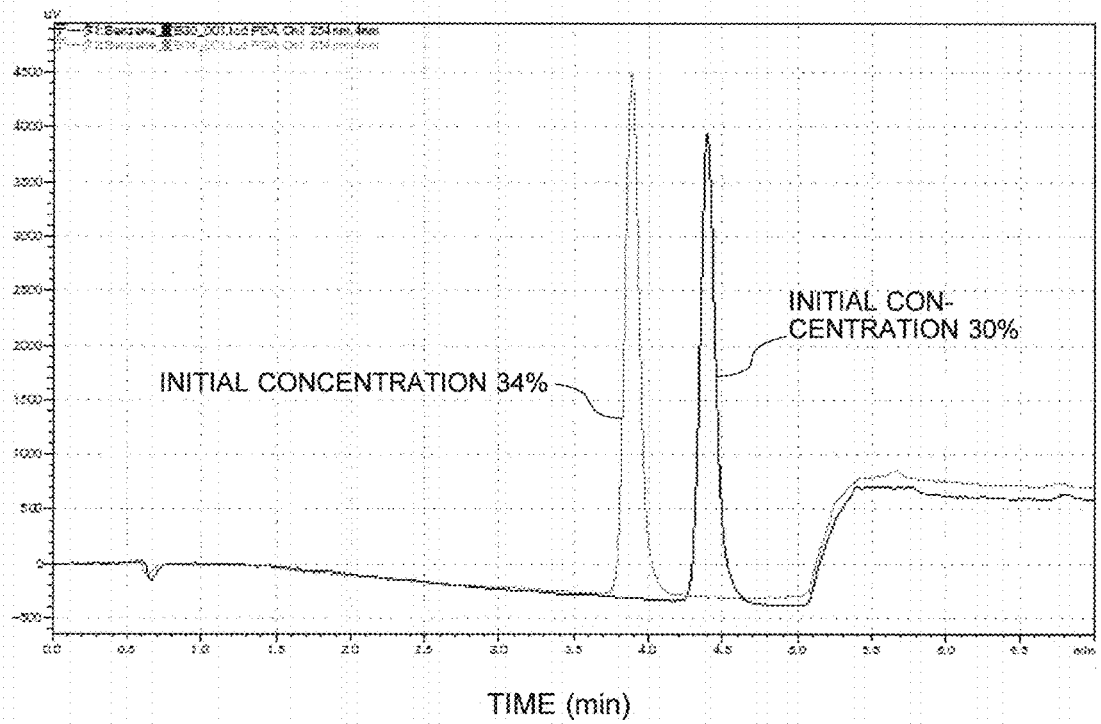
FIG. 8 shows a table (a) and chromatogram (b) illustrating the relationship between the initial concentration of the mobile phase and the retention time, with benzene as the sample.
Figure 9:
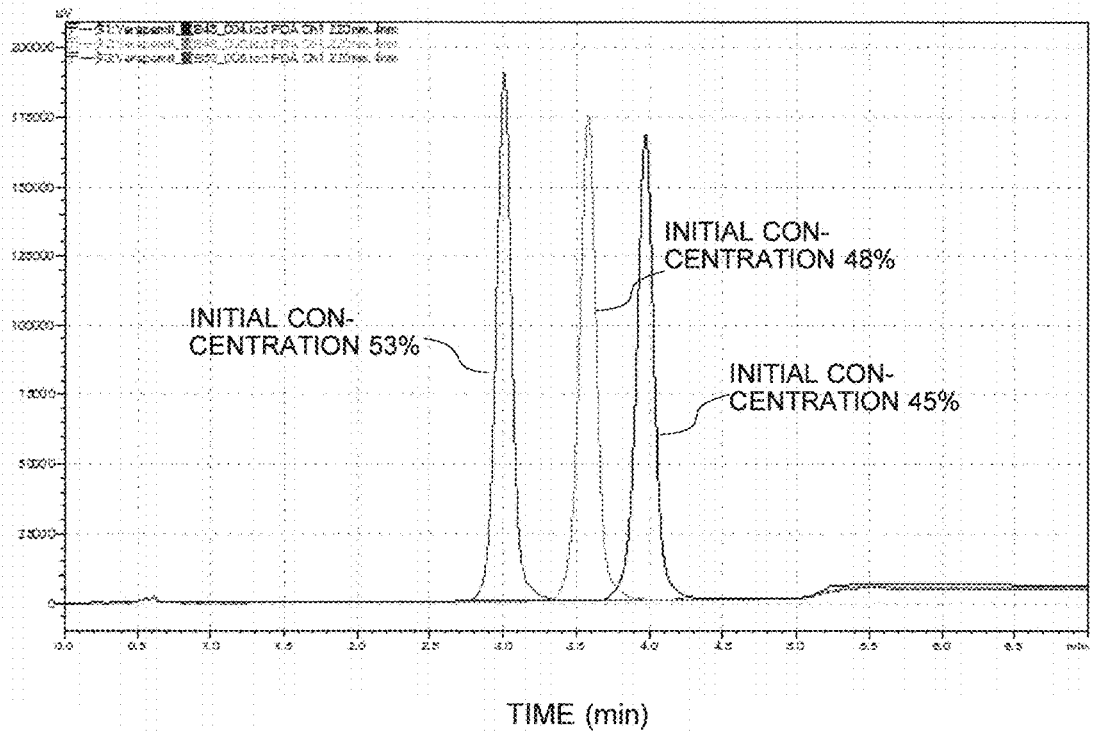
FIG. 9 shows a table (a) and chromatogram (b) illustrating the relationship between the initial concentration of the mobile phase and the retention time, with verapamil as the sample.
Figure 10:
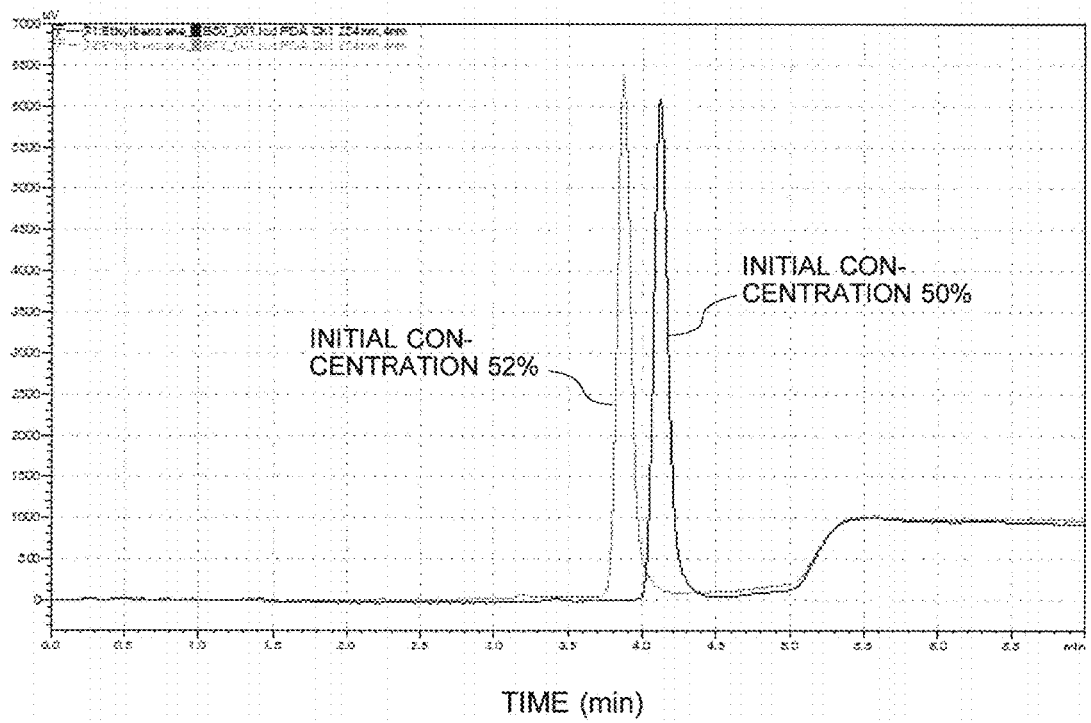
FIG. 10 shows a table (a) and chromatogram (b) illustrating the relationship between the initial concentration of the mobile phase and the retention time, with ethylbenzene as the sample.
Figure 11:
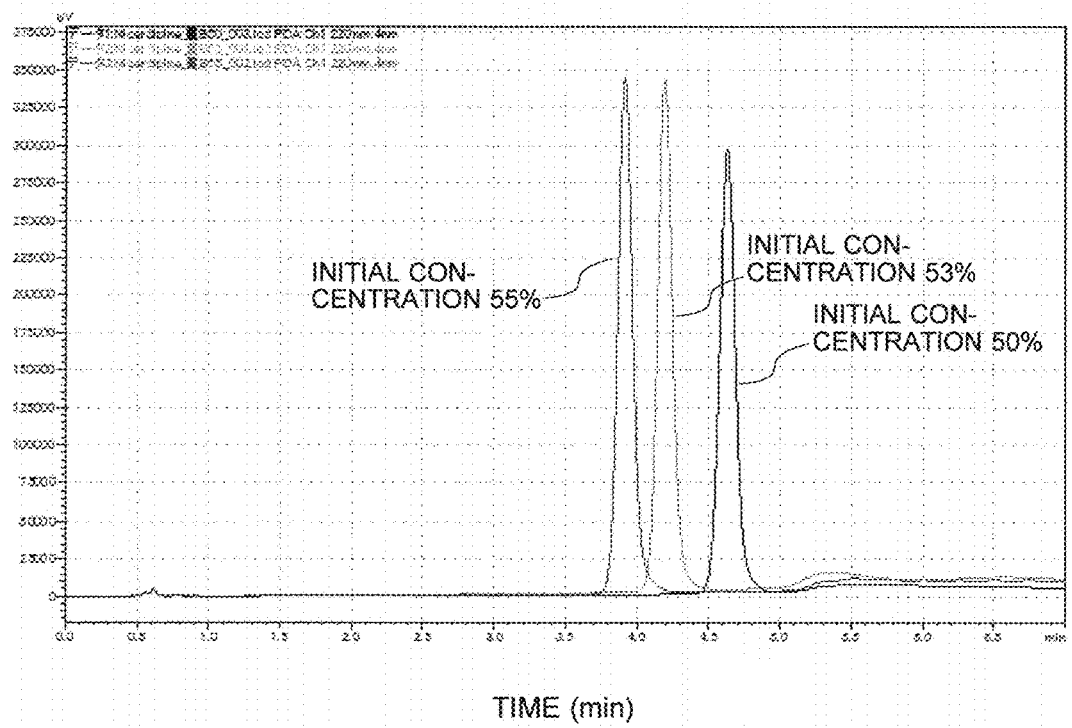
FIG. 11 shows a table (a) and chromatogram (b) illustrating the relationship between the initial concentration of the mobile phase and the retention time, with nicardipine as the sample.

FIG. 3A shows a chromatogram obtained as a result of an LC analysis in the preparative separation condition searching mode performed under the conditions shown in FIGS. 2A and 2B for a sample containing six compounds (nicardipine, verapamil, phenol, benzene, ethylbenzene and 2,6-dimethylaniline). FIG. 3B shows the retention time of each compound determined from the chromatogram.

In the controlling and processing unit 20, necessary information for determining the preparative separation conditions is stored in the form of a database. The controlling and processing unit 20 refers to this database to determine preparative separation conditions. The necessary information for determining the preparative separation conditions is organized for each standard sample or compound in the form of a database, in which the following data are related to the preparative separation conditions: chromatogram data of the LC analysis in the preparative separation condition searching mode previously performed using the preparative separation LC 1 for standard samples, and chromatogram data of the LC analysis in the preparative separation mode previously performed using the preparative separation LC 1 for the same standard samples. For example, with regard to the initial concentration of the mobile phase, which is one of the preparative separation conditions, a computing equation for calculating the concentration from the retention time of each component determined from the chromatogram data obtained by the LC analysis in the preparative separation condition searching mode is stored and related to the target elution time. Using this computing equation, the controlling and processing unit 20 determines the initial concentration of the mobile phase from the retention time obtained by the LC analysis in the preparative separation condition searching mode performed for the target sample.

FIG. 4 shows a computing equation expressing the relationship between the retention time of a component contained in a target sample in the LC analysis in the preparative separation condition searching mode and the initial concentration of the mobile phase in the LC analysis in the preparative separation mode for the same target sample, as well as a graph representing the same equation.

In the computing equation in FIG. 4, $Y=89.161X-79.11$, X represents the retention time of a component contained in the target sample in the preparative separation condition searching mode, and Y represents the initial concentration of the mobile phase in the preparative separation mode. By this computing equation, the initial concentration of the mobile phase in the preparative separation mode can be calculated from the retention time of the target component in the LC analysis of the target sample in the preparative separation condition searching mode. A method for deriving the computing equation will be described later.

After the preparative separation conditions have been determined in this manner, when the preparative separation mode is set by an operation on the operation unit 22 by the user and a command for initialing the LC analysis is issued, the passage switching valves 8c and 8d are switched, and the liquid-sending pumps 4, 5 and other elements are operated according to the set preparative separation conditions, whereby the sample is introduced into the preparative separation column 8b along with the mobile phase. The sample components separated by the preparative separation column 8b are detected by the first detector 9. Based on the detection signals, the operation of the fraction collector is controlled so that each component in the sample is separately collected.

Hereinafter described is a method for deriving the computing equation used for determining the initial condition of the mobile phase (initial concentration of acetonitrile), which is a preparative separation condition, from the retention time obtained in the LC analysis in the preparative separation condition searching mode. For the present description, it is assumed that the chromatograms and retention times as shown in FIGS. 3A and 3B have been obtained as a result of the LC analysis in the preparative separation condition searching mode for standard samples containing the six components listed in FIG. 3B.

Initially, an LC analysis in the preparative separation mode for the aforementioned standard samples is performed under the preparative separation conditions shown in FIG. 5A and according to the liquid-sending schedule shown in FIG. 5B. In FIG. 5B, X represents the initial concentration of the acetonitrile contained in the mobile phase. The preparative separation conditions and liquid-sending schedule may be set by the user, or they may be previously stored in the controlling and processing unit 20.

This LC analysis is performed several times using different values of the initial concentration of the acetonitrile. Each time, a chromatogram is created from the detection signals of the first detector 9, and a set of data in which the retention time is located near the previously set target elution time is collected. Although the retention time may be arbitrarily set, setting a longer retention time consumes a larger amount of mobile phase during the preparative separation while no additional improvement in the separating performance can be expected. Accordingly, it is preferable to set an appropriate retention time for the column used in the preparative separation mode so that the k value (a retention index in the chromatogram) will not be greater than 10. In the present embodiment, on the assumption that the k value as the retention index should be five, the retention time is set at four minutes.

Each of FIGS. 6-11 shows a table (a) and chromatogram (b) illustrating the initial concentration of the mobile phase with which the elution time of the compound concerned was located near four minutes. From these results, the initial concentration of the mobile phase (acetonitrile) which gives an elution time of four minutes is calculated from the following approximate equation (1):

$$\text{Approximate equation: } Y = \alpha X + \beta \tag{1}$$

where, X represents the elution time, and Y represents the initial concentration of the mobile phase at that time. The constants $\alpha$ and $\beta$ represent numerical values determined by substituting, into the equation, the elution times and initial concentrations actually obtained for each compound. The values of $\alpha$ and $\beta$ can be calculated if there are at least two sets of data of the elution time and initial concentration for each compound.

FIG. 12 shows: the retention time obtained by the LC analysis in the preparative separation condition searching mode for the six compounds; the elution time obtained by the LC analysis in the preparative separation mode, along with the initial concentration of acetonitrile used in the analysis; the values of $\alpha$ and $\beta$ in the approximate equation (1); and the initial concentration of acetonitrile, calculated from the approximate equation, with which the target elution time (four minutes) is obtained.

Subsequently, a computing equation is derived which expresses the relationship between the retention time obtained in the LC analysis in the preparative separation condition searching mode performed for the six compounds and the initial concentration of acetonitrile, calculated from the approximate equation (1), with which the target elution time is obtained. This computing equation can be estimated by creating a graph with the X axis representing the retention time and the Y axis representing the initial concentration of acetonitrile, and finding a function that fits to this graph. FIG. 4 shows a graph and computing equation created in this manner. In FIG. 4, R2 (coefficient of determination, which is the square of the correlation coefficient R) is an index indicating the validity of the computing equation. The closer to 1 this value is, the more accurate the transition from the preparative separation condition searching mode to the preparative separation mode can be.

The present invention is not limited to the previous embodiment.

For example, in the previous embodiment, after the retention time is obtained in the preparative separation condition searching mode, the retention time is substituted into the computing equation shown in FIG. 4 to calculate the initial concentration of the mobile phase in the LC analysis in the preparative separation mode, and subsequently, the liquid-sending schedule shown in FIG. 5B is set based on the calculated initial concentration. It is also possible to modify the preparative conditions, such as the composition of the mobile phase or liquid-sending schedule, depending on the amount (length) of retention time obtained in the preparative separation condition searching mode.

Specifically, for a component whose retention time obtained in the preparative separation condition searching mode in the previous embodiment is greater than 1.78 minutes, the initial concentration of the mobile phase in the LC analysis in the preparative separation mode, calculated from the computing equation shown in FIG. 4, will exceed 80%. In this case, using the liquid-sending schedule shown in FIG. 5B is inappropriate, because the mobile-phase concentration at the target elution time (four minutes) exceeds the upper limit of 100%. Additionally, in such a case, even if the mobile-phase concentration at the target elution time is set at 100%, the target component may not be eluted from the column before the target elution time. Accordingly, in such a case, the liquid-sending schedule and/or mobile-phase composition may be modified so that the elution power will be stronger than in the case of the preparative separation conditions and liquid-sending schedule shown in FIGS. 5A and 5B.

For a component whose retention time obtained in the preparative separation condition searching mode in the previous embodiment is less than 0.88 minutes, the initial concentration of the mobile phase in the LC analysis in the preparative separation mode, calculated from the computing equation shown in FIG. 4, will fall below the lower limit of 0%, which is also inappropriate. In this case, it might be possible to set the initial concentration of the mobile phase in the liquid-sending schedule shown in FIG. 5B at 0% and perform the LC analysis in the preparative separation mode. However, in this case, it is most likely that the target component is eluted from the column earlier than the target elution time. Accordingly, in such a case, the liquid-sending schedule and/or mobile-phase composition may be modified so that the elution power will be weaker than in the case of the preparative separation conditions and liquid-sending schedule shown in FIGS. 5A and 5B.

The previously described operation of modifying the liquid-sending schedule and/or mobile-phase composition according to the amount of retention time obtained in the preparative separation condition searching mode is one possible mode for carrying out the process in which "the preparative separation conditions for a component contained in the target sample are determined based on the chromatogram data of the target sample and the index, with reference to the database" in the present invention. Such a mode enables the preparative separation of target components whose hydrophobicity widely ranges from high to low degrees.

The previously described example was concerned with the case of modifying the liquid-sending schedule and/or mobile-phase composition. Additionally, for example, the flow rate of the mobile phase, amount of injection of the sample, or capacity of the column may also be modified. It is also possible to modify two or more kinds of preparative separation conditions.

Using a computing equation is not always necessary; the preparative separation conditions may also be determined by searching the database in the controlling and processing unit 20 for a standard sample whose chromatogram data are similar to the chromatogram obtained for the target sample in the preparative separation condition searching mode, extracting the preparative separation conditions corresponding to the target elution time from the chromatogram data in the preparative separation mode of that standard sample, and adopting the extracted conditions as the preparative separation conditions for the target sample.

In the previous embodiment, the relationship between the retention time in the LC analysis in the preparative separation condition searching mode and the initial concentration of the mobile phase in the LC analysis in the preparative separation mode is expressed by a single computing equation (see FIG. 4). It is also possible to set a plurality of computing equations according to the natures of the compounds as the target components. The "nature" in this case means a nature that affects the component separation by the chromatograph analysis.

Hereinafter described as one example is the case in which the compounds are divided into three classes according to their degree of affinity to water, with different computing equations respectively set for the three classes of compounds. FIG. 13 shows computing equations expressing the relationship between the retention time in the LC analysis in the preparative separation condition searching mode (horizontal axis) and the initial concentration of the mobile phase in the LC analysis in the preparative separation mode (vertical axis) for the three classes of compounds, as well as a graph representing those computing equations. In the graph shown in FIG. 13, the left area represents the computing equation for compounds with extremely high degrees of hydrophilicity, while the graph in the right area represents the computing equation for compounds with extremely high degrees of hydrophobicity. The graph in the middle area represents the computing equation for compounds with intermediate natures. The computing equation in the middle area is applied to many compounds with normal degrees of affinity to water, while those in the left and right areas are applied to compounds which are not included in the group of normal compounds.

Figure 14:
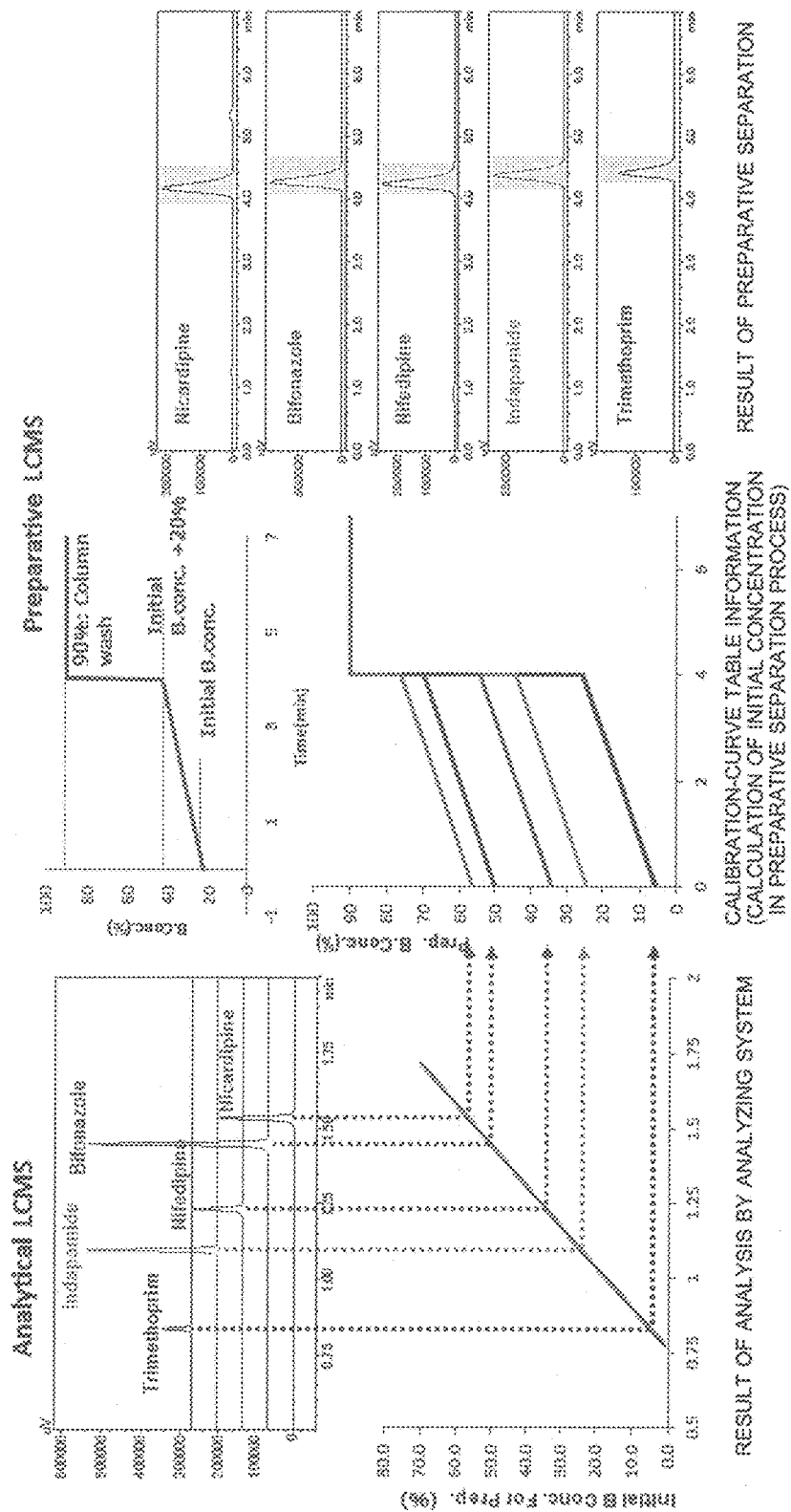
FIG. 14 shows, for five compounds, the relationship among the retention time obtained by the LC analysis in the preparative separation condition searching mode, initial concentration of the mobile phase calculated from the computing equations shown in FIG. 13, and chromatogram of each compound obtained when the LC analysis in the preparative separation mode is performed using the calculated initial concentration.

FIG. 14 shows the relationship among the retention time obtained in the LC analysis in the preparative separation condition searching mode, initial concentration of the mobile phase calculated from the computing equations shown in FIG. 13, and chromatogram obtained by performing the LC analysis in the preparative separation mode using the calculated initial concentration, for five compounds: nicardipine, bifonazole, nifedipine, indapamide and trimethoprim. These five compounds are all compounds included in the middle area in FIG. 13. FIG. 14 demonstrates that all of these compounds have their retention times located near four minutes.

As in the previously described embodiment, when a single computing equation is applied to all compounds, the initial concentration of the mobile phase calculated from the computing equation may possibly exceed the upper limit (100%) or fall below the lower limit (0%). Such a problem can be decreased by grouping the compounds based on their natures which affect the component separation in the LC analysis, and setting an appropriate computing equation for each nature. Consequently, the initial concentration of the mobile phase in the LC analysis in the preparative separation mode can be calculated with a high level of accuracy for a wide variety of compounds.

REFERENCE SIGNS LIST

4 . . . First Liquid-Sending Pump
5 . . . Second Liquid-Sending Pump
7 . . . Injector
8 . . . Separation Column
8a . . . Preparative Separation Condition Search Column
8b . . . Preparative Separation Column
8c, 8d . . . Passage Switching Valve
9 . . . First Detector
10 . . . Fraction Collector
11 . . . Second Detector
20 . . . Controlling and Processing Unit
21 . . . Display Unit
22 . . . Operation Unit

The invention claimed is:

1. A preparative separation liquid chromatograph system for controlling an operation of a preparative separation liquid chromatograph in which a sample temporally separated into components by a liquid chromatograph analysis is introduced into a detector and a fraction collector, with each component fractionated and collected by the fraction collector based on a result of a detection by the detector, the system comprising:
   a) a chromatographing section having a preparative separation analysis mode for performing a liquid chromatograph analysis using a column for preparative separation and a preparative separation condition searching mode for performing a liquid chromatograph analysis using a column for searching for a preparative separation condition having a different capacity from the column for preparative separation;
   b) a chromatogram creating section for creating a chromatogram based on a detection signal from the detector;
   c) a standard sample database section for storing in a memory following data on various standard samples for each sample or compound in a form of a database: chromatogram data obtained when the liquid chromatograph analysis in the preparative separation condition searching mode is performed under a predetermined search condition; and chromatogram data obtained when the liquid chromatograph analysis in the preparative separation analysis mode is performed for the various standard samples under one or a plurality of sets of preparative separation conditions, along with the preparative separation condition used in this analysis;
   d) an index input section for allowing a user to input an index for a target sample, the index used for determining the preparative separation condition used when separating the target sample into components by the liquid chromatograph analysis in the preparative separation analysis mode and separately collecting each component; and
   e) a preparative separation condition determining section for making the chromatographing section perform the liquid chromatograph analysis in the preparative separation condition searching mode for the target sample under the predetermined search condition, and for determining the preparative separation condition for a component contained in the target sample, based on the chromatogram data obtained by this analysis and the aforementioned index, with reference to the database.

2. The preparative separation liquid chromatograph system according to claim 1, wherein the preparative separation condition is an initial condition of a mobile phase introduced into a column along with a sample.

3. The preparative separation liquid chromatograph system according to claim 1, wherein:
   the standard sample database section stores in the memory, in the form of the database, an elution beginning time of each component determined from the chromatogram data obtained by the liquid chromatograph analysis in the preparative separation analysis mode performed for various standard samples, along with the preparative separation condition used in this analysis; and
   the index input section allows a user to input a target elution beginning time as the index.

4. The preparative separation liquid chromatograph system according to claim 3, wherein the preparative separation condition is an initial condition of a mobile phase introduced into a column along with a sample.

5. The preparative separation liquid chromatograph system according to claim 3, wherein:
the standard sample database section holds a computing equation for determining the preparative separation condition corresponding to the elution beginning time, from a retention time of each component and the elution beginning time, the retention time determined from the chromatogram data obtained by the liquid chromatograph analysis in the preparative separation condition searching mode performed for various standard samples; and
the preparative separation condition determining section determines the retention time of each component in the target sample from the chromatogram data obtained by the liquid chromatograph analysis in the preparative separation condition searching mode performed for the target sample, and determines the preparative separation condition for the target sample from the retention time and the index, using the computing equation.

6. The preparative separation liquid chromatograph system according to claim 5, wherein the preparative separation condition is an initial condition of a mobile phase introduced into a column along with a sample.

7. A preparative separation condition searching method for searching for a preparative separation condition used in a process in which a sample temporally separated into components by a liquid chromatograph analysis is introduced into a detector and a fraction collector, with each component fractionated and collected by the fraction collector based on a result of a detection by the detector; the method comprising:
a) a standard sample database storage process in which following data on various standard samples are stored in a memory for each sample or compound in a form of a database: chromatogram data obtained when a liquid chromatograph analysis in a preparative separation analysis mode using a column for preparative separation is performed; and chromatogram data obtained when a liquid chromatograph analysis in a preparative separation condition searching mode using a column for searching for a preparative separation condition having a different capacity from the column for preparative separation is performed;
b) an index input process in which a user is allowed to input an index for a target sample, the index used for determining the preparative separation condition used when separating the target sample into components by the liquid chromatograph analysis in the preparative separation analysis mode and for separately collecting each component;
c) a data obtaining process in which the liquid chromatograph analysis in the preparative separation condition searching mode is performed for the target sample to obtain chromatogram data of the target sample; and
d) a preparative separation condition determining process in which the preparative separation condition for a component contained in the target sample is determined based on the chromatogram data of the target sample and the aforementioned index, with reference to the database.

8. The preparative separation condition searching method according to claim 7, wherein the preparative separation condition is an initial condition of a mobile phase introduced into a column along with a sample.

9. The preparative separation condition searching method according to claim 7, wherein:
the standard sample database storage process comprises storing, in the form of the database, an elution beginning time of each component determined from a chromatogram data obtained by the liquid chromatograph analysis in the preparative separation analysis mode performed for various standard samples, along with the preparative separation condition used in this analysis; and
the index input process comprises allowing a user to input a target elution beginning time as the index.

10. The preparative separation condition searching method according to claim 9, wherein the preparative separation condition is an initial condition of a mobile phase introduced into a column along with a sample.

11. The preparative separation condition searching method according to claim 9, wherein:
the standard sample database storage process comprises holding a computing equation for determining the preparative separation condition corresponding to the elution beginning time, from a retention time of each component and the elution beginning time, the retention time determined from the chromatogram data obtained by the liquid chromatograph analysis in the preparative separation condition searching mode performed for various standard samples; and
the preparative separation condition determining process comprises determining the retention time of each component in the target sample from the chromatogram data obtained by the liquid chromatograph analysis in the preparative separation condition searching mode performed for the target sample, and determining the preparative separation condition for the target sample from the retention time and the index, using the computing equation.

12. The preparative separation condition searching method according to claim 11, wherein the preparative separation condition is an initial condition of a mobile phase introduced into a column along with a sample.

* * * * *